US 8,105,304 B2

United States Patent
Uda

(12) United States Patent
(10) Patent No.: US 8,105,304 B2
(45) Date of Patent: Jan. 31, 2012

(54) FOLDED DISPOSABLE PANTS

(75) Inventor: Masashi Uda, Osaka (JP)

(73) Assignee: Livedo Corporation, Ehime (JP)

( * ) Notice: Subject to any disclaimer, the term of this patent is extended or adjusted under 35 U.S.C. 154(b) by 154 days.

(21) Appl. No.: 12/459,563

(22) Filed: Jul. 2, 2009

(65) Prior Publication Data

US 2009/0299321 A1 Dec. 3, 2009

Related U.S. Application Data

(63) Continuation of application No. 10/557,959, filed as application No. PCT/JP03/07844 on Jun. 20, 2003.

(51) Int. Cl.
*A61F 13/15* (2006.01)
*B29C 65/00* (2006.01)
*B31B 1/00* (2006.01)
*B31B 1/26* (2006.01)

(52) U.S. Cl. ..... 604/385.201; 604/385.01; 604/385.101; 156/164; 156/204; 493/405; 493/394

(58) Field of Classification Search ............. 604/385.01, 604/385.101, 385.201; 156/164, 204; 493/405, 493/394

See application file for complete search history.

(56) References Cited

U.S. PATENT DOCUMENTS

| | | | |
|---|---|---|---|
| 3,963,029 A | 6/1976 | Brooks | |
| 3,973,567 A | 8/1976 | Srinivasan et al. | |
| 4,781,712 A | 11/1988 | Barabino et al. | |
| 5,037,417 A | 8/1991 | Ternstroem et al. | |
| 5,569,228 A | 10/1996 | Byrd et al. | |
| 6,260,211 B1 | 7/2001 | Rajala et al. | |
| 6,297,424 B1 | 10/2001 | Olson et al. | |
| 6,478,786 B1 | 11/2002 | Glaug et al. | |
| 6,502,695 B1 | 1/2003 | Kim et al. | |
| 6,569,139 B1 | 5/2003 | Datta et al. | |
| 6,595,976 B2 | 7/2003 | Jitoe et al. | |
| 6,761,013 B2 | 7/2004 | Tippey et al. | |
| 7,135,013 B2 | 11/2006 | Olson et al. | |
| 7,150,137 B2 | 12/2006 | Tippey | |
| 7,237,370 B1 | 7/2007 | Garone et al. | |

(Continued)

FOREIGN PATENT DOCUMENTS

EP 1 547 562 6/2005

(Continued)

OTHER PUBLICATIONS

U.S. Appl. No. 10/557,959, filed Nov. 22, 2005, Uda.

(Continued)

*Primary Examiner* — Jacqueline F. Stephens
(74) *Attorney, Agent, or Firm* — Cermak Nakajima LLP; Tomoko Nakajima

(57) ABSTRACT

Folded disposable pants which include an outer wear sheet of pants shape and an absorbent main body adhered to a skin-contacting surface side in the outer wear sheet, wherein elastic members are added at least to circumferences of a waist opening and a leg opening. The folded disposable pants are formed by folding back a crotch part of the disposable pants over a center pants part on the upside of the crotch part, folding back a left lateral part and a right lateral part of the pants over the center pants part, and then folding back an upper pants part in which the left and the right lateral parts of the pants are overlapped with each other, over a downside part thereof.

6 Claims, 8 Drawing Sheets

U.S. PATENT DOCUMENTS

| | | | |
|---|---|---|---|
| 7,419,562 | B2 | 9/2008 | Van Gompel et al. |
| 7,431,791 | B2 | 10/2008 | Heller et al. |
| 2002/0055430 | A1* | 5/2002 | Coenen et al. .............. 493/418 |
| 2002/0072728 | A1 | 6/2002 | Shinohara et al. |
| 2002/0156441 | A1 | 10/2002 | Sawyer et al. |
| 2003/0036739 | A1 | 2/2003 | Christoffel et al. |
| 2004/0078018 | A1 | 4/2004 | Gompel et al. |
| 2004/0167460 | A1 | 8/2004 | Anderson et al. |
| 2004/0167489 | A1 | 8/2004 | Dellenberger et al. |
| 2004/0168947 | A1 | 9/2004 | McDonald |
| 2005/0027272 | A1 | 2/2005 | Suzuki et al. |

FOREIGN PATENT DOCUMENTS

| | | |
|---|---|---|
| JP | 61-30670 | 2/1986 |
| JP | 3-21238 | 1/1991 |
| JP | 9-110019 | 4/1991 |
| JP | 3-113004 | 5/1991 |
| JP | 4-000828 | 1/1992 |
| JP | 6-000204 | 1/1994 |
| JP | 3021190 | 11/1995 |
| JP | 3032998 | 10/1996 |
| JP | 9-110020 | 4/1997 |
| JP | 9-131364 | 5/1997 |
| JP | 10-095481 | 4/1998 |
| JP | 3055348 | 10/1998 |
| JP | 11-113956 | 4/1999 |
| JP | 2000-024029 | 1/2000 |
| JP | 2000-024030 | 1/2000 |
| JP | 2000-042029 | 2/2000 |
| JP | 2001-019070 | 1/2001 |
| WO | WO-01/89439 | 11/2001 |

OTHER PUBLICATIONS

Definition of "yarn", Webster's Third new International Dictionary, Unabridged, Copyright 1993 Merriam-Webster, Incorporated. Published under license from Merriam-Webster, Incorporated. Literature Online Reference Edition—Reference Shelf: Full Text http://lionreference.chadwyck.com/searchFulltext.do?id=40475506&idType=offset&divLevel=2&...Jun. 14, 2010.

* cited by examiner (a)

FOLDED DISPOSABLE PANTS

This is a Continuation Application of Ser. No. 10/557,959 filed Nov. 22, 2005.

BACKGROUND OF THE INVENTION

The present invention relates to folded disposable pants which are preformed into a pants shape, and more particularly, to folded disposable pants which are suited for large adult-sized pants.

DESCRIPTION OF THE RELATED ART

FIG. 8 is a front view of conventional disposable pants. In these disposable pants, to an outer wear sheet 50 formed into a pants shape by providing an waist opening W and leg openings S, S, there are added an waist elastic member 51, a leg elastic member 52, and a body fitting elastic member 53, and an absorbent main body 54 is adhered to a skin-contactable surface side of the outer wear sheet.

Longitudinal ends of the absorbent main body 54 contract toward the center of the pants through contraction force of the body fitting elastic member 53. In the right and left lateral side parts of the pants where the absorbent main body is not disposed, contraction force of the body fitting elastic member 53 gives gathers and provides fluffy condition.

The absorbent main body 54 of the conventional disposable pants has a structure where a water-absorbent core formed of pulp fiber and superabsorbent polymer powder is disposed between a water-impermeable film and a water-permeable nonwoven fabric. Due to the existence of the pulp fiber, it is formed so as to have rough and thick appearance.

In order to improve the portability in bringing back, the disposable pants are desirably packed in a compact package, and therefore, the disposable pants should be folded. Because of the bulky absorbent main body 54 and deformation through contraction force of the body fitting elastic member 53, the above conventional disposable pants are folded in such a manner that right and left lateral parts of the pants are folded back over the center part of the pants along folding lines L1 and L2 shown in FIG. 8 to give a shape as shown in FIG. 9, and then an upper part of a folding line L3 is folded back over a lower part to give a trapezoidal shape as shown in FIG. 10(a).

As seen from the schematic side view of the folded pants in FIG. 10(b), the bulky absorbent main body 54 is folded in four, so that a large difference in thickness arises between the lower part where the absorbent main body 54 is folded and the upper part where only the outer wear sheet 50 is present. In the case of a folding structure having parts with different thicknesses, the disposable pants of such a folding structure are inferior in handling ability when put in a package, leading the problems that good packaging is impossible and each package is not well self-organized.

In addition, in the case of adult disposable pants, when the above folding structure is employed, the thickness will be 6 to 8 cm and the width and the length will be as large as about 20 cm even in a folded state. Therefore, when a user desires to carry it when going out, the bulky profile is quite unfavorable.

In consideration of the above problems, it is an object of the present invention to provide folded disposable pants in a compact and non-bulky manner which is suited for a user to carry.

SUMMARY OF THE INVENTION

The subject matter of the present invention is disposable pants which comprise an outer wear sheet of pants shape and an absorbent main body adhered to a skin-contactable surface side of the outer wear sheet, in which a waist elastic member and a leg elastic member are added to circumferences of an waist opening and a leg opening, respectively, in a back section of the disposable pants, a body fitting elastic member is added in the same direction as the waist elastic member between a longitudinal end edge of the absorbent main body and the waist elastic member, in a front section of the disposable pants, a body fitting elastic member is not added, and the folded pants are formed by folding back a crotch part of the disposable pants over a center pants part on the upside of the crotch part, folding back a left lateral part and a right lateral part of the pants over the center pants part respectively, and then folding back an upper pants part in which the left and the right lateral parts of the pants are overlapped with each other, over a downside part thereof.

By employing the above folding structure, it is possible to compactly fold disposable pants.

In the above folded disposable pants, the absorbent main body of the disposable pants may has a thickness of 5 mm or smaller.

In the above folded disposable pants, at least both ends in the longitudinal direction of the absorbent main body may be formed into a substantially rectangular shape, and further, the left and the right lateral parts of the disposable pants may be respectively folded back along a left lateral line and a right lateral line of the absorbent main body.

In the above folded disposable pants, a body fitting elastic member may be added in the same direction as the waist elastic member between a longitudinal end edge of the absorbent main body and the waist elastic member in one or both of a front section and a back section of the disposable pants.

In the above folded disposable pants, the absorbent main body of the disposable pants may be adhered to the outer wear sheet so that a length between a lowermost end of the crotch part of the disposable pants and a longitudinal end of the absorbent main body may be approximately twice the length between the longitudinal end of the absorbent main body and the end of the waist opening, and further, the disposable pants may be folded into approximately one third of the length between the end of the waist opening and the lowermost end of the crotch part of the disposable pants.

DETAILED DESCRIPTION OF THE PREFERRED EMBODIMENTS

Figure 1:
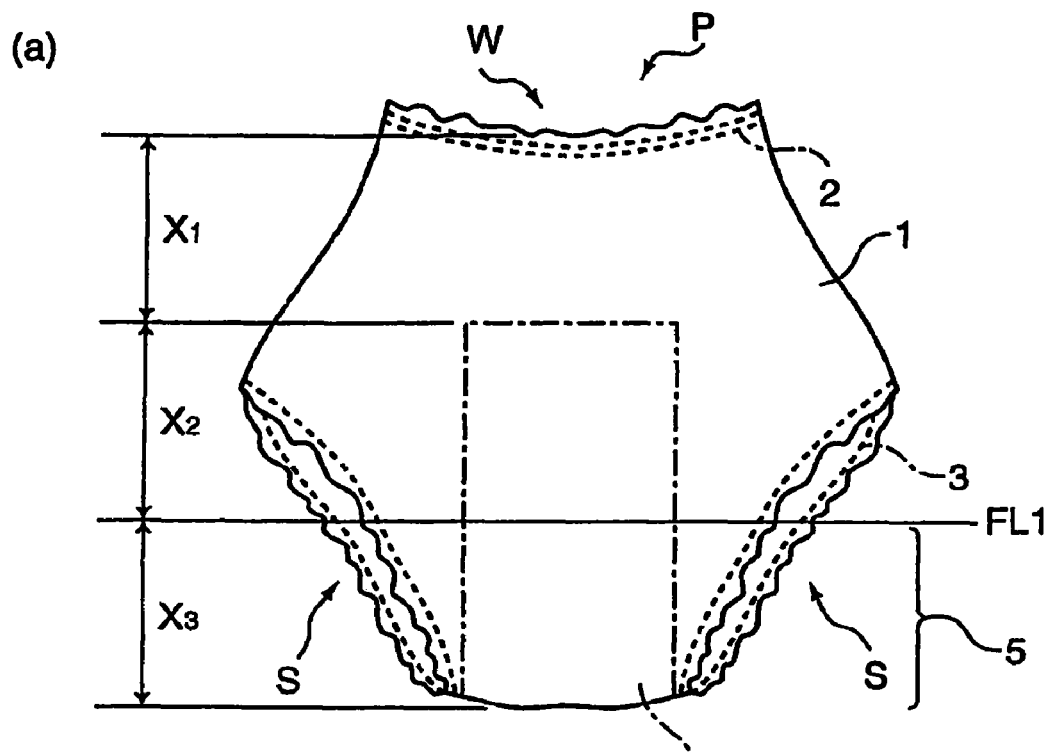
FIG. 1(a) is a front view of disposable pants before folded.
FIG. 1(b) is a front view for explaining a first folding step.
Figure 1:
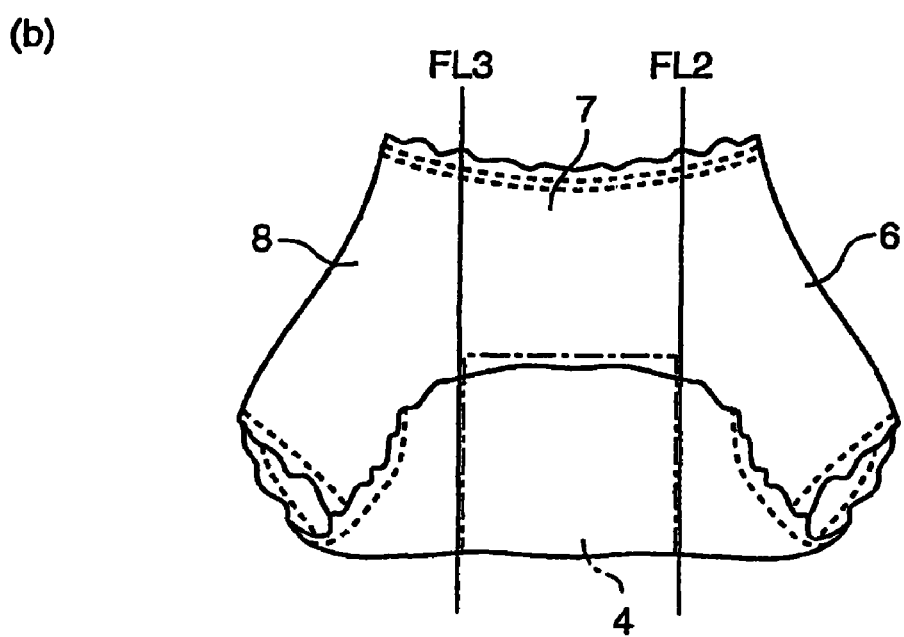

Folded disposable pants according to the present invention will be explained below by reference to the drawings attached hereto. FIG. 1(a) shows disposable pants P before folded. The disposable pants P has a pants shape formed by providing an outer wear sheet 1 with a waist opening W and a leg opening S. To the circumferences of the waist opening W and the leg opening S, a waist elastic member 2 and a leg elastic member 3 are respectively added in an elongated state to give gathers. To each surface side of the outer wear sheet 1 being contactable with wearer's skin, an absorbent main body 4 is adhered.

A crotch part 5 of the disposable pants is folded back along a line FL1 upward to give a shape as shown in FIG. 1(b) (first folding step). At this time, a length $x_3$ of the crotch part 5 is desirably one third of the length $(x_1+x_2+x_3)$ from the lowermost end of the crotch part to a waist opening end of the disposable pants. Also a length $x_1$ between an end line of the absorbent main body 4 in the longitudinal direction and the waist opening end is preferably one third of $(x_1+x_2+x_3)$. In other word, it is preferred that $x_1$, $x_2$, and $x_3$ are approximately equal to one another. With this constitution, the absorbent main body 4 is folded in two both in the front section and in the back section, and eventually it can be folded into approximately one third of the length between the waist opening end and the lowermost end of the crotch part of the disposable pants, giving beautiful appearance of the folded form.

Figure 2:
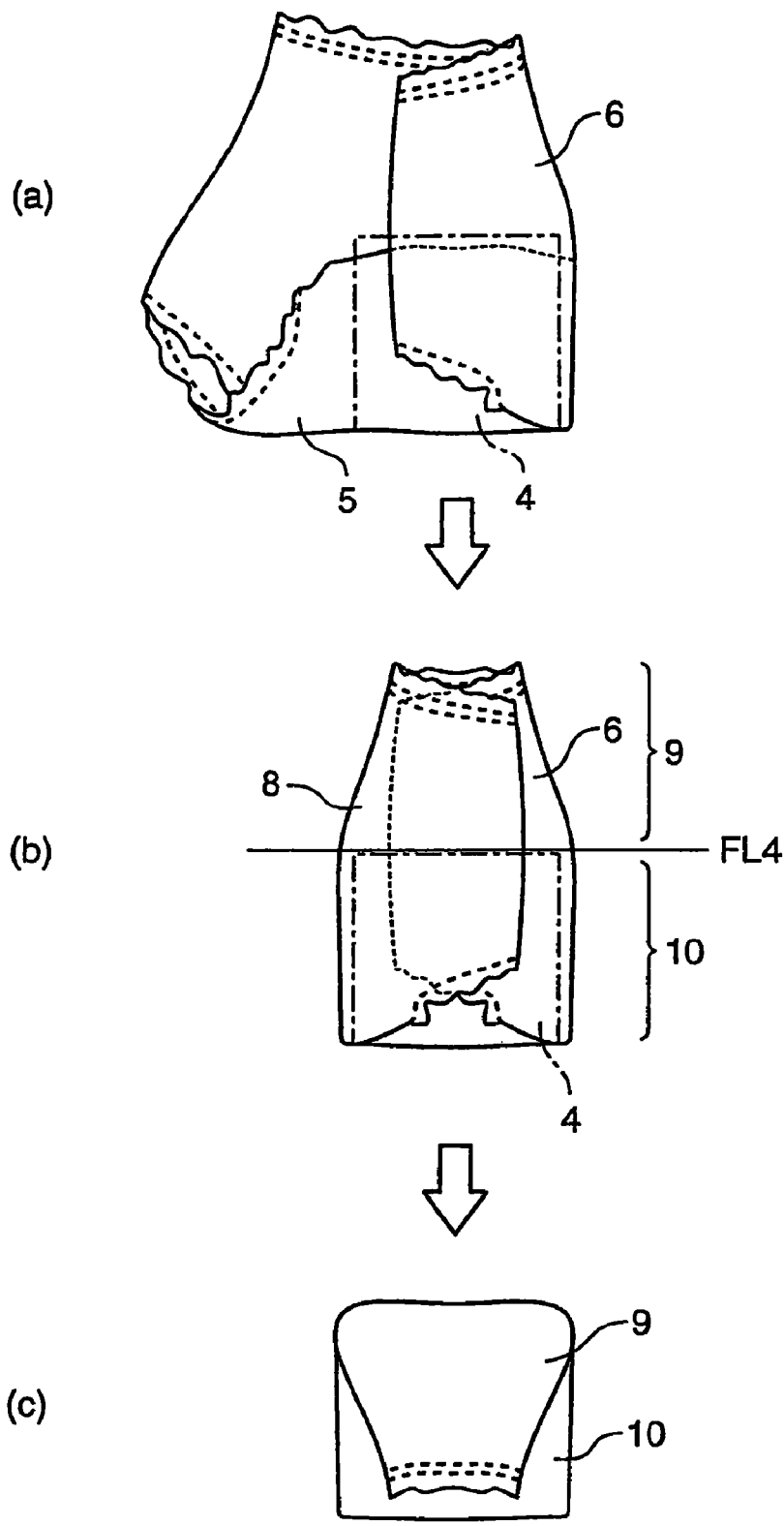
FIGS. 2(a) to 2(c) are front views for explaining second to fourth folding steps.

Then, a right lateral pants part 6 on the right of the absorbent main body 4 is folded back over a center pants part 7 along a line FL2 which aligns with the right lateral end of the absorbent main body 4 (second folding step) to give a shape shown in FIG. 2(a). In the same manner, a left lateral pants part 8 on the left of the absorbent main body 4 is folded back over the pants center pants part 7 along a line FL3 which aligns with the left lateral end of the absorbent main body 4 (third folding step) to give a shape shown in FIG. 2(b).

Finally, an upper pants part 9 is folded over a lower part 10 along a line FL 4 which aligns with an end edge of the absorbent main body 4. The lower part 10 is a part resulting from folding back the right and left lateral pants parts 6, 8 over the pants crotch part 5 (fourth folding step).

Thus, all of the folding steps are completed. By these folding steps, it is possible to fold pants into a quadrilateral having a length of about one third of the entire length of the front section (or back section) before folded and a width approximately equal to that of the absorbent main body 4. In the conventional folding structure, pants can be folded into at most a half size of the front section before folded and distortion will occur in the shape of the folded pants; however, according to the present invention, pants can be folded into a compact quadrilateral and the portability is improved. In the case of disposable pants having a disposal tape in a center part of the front section or back section, by folding the pants so that the side that bears the disposal tape is on the front side in FIG. 1, the disposal tape will be hidden by the right and left lateral pants parts 6, 8 or the upper pants part 9 and will not be exposed after completion of the folding. Therefore, it is possible to prevent a trouble such as removal of the tape from occurring during packaging.

The order of the first folding step, and the second and third folding steps may be inverted, and in such a case, the crotch part 5 may be folded back over the center pants part 7 after folding back the right and left lateral pants parts 6, 8 (in any order) over the center pants part 7.

Figure 3:
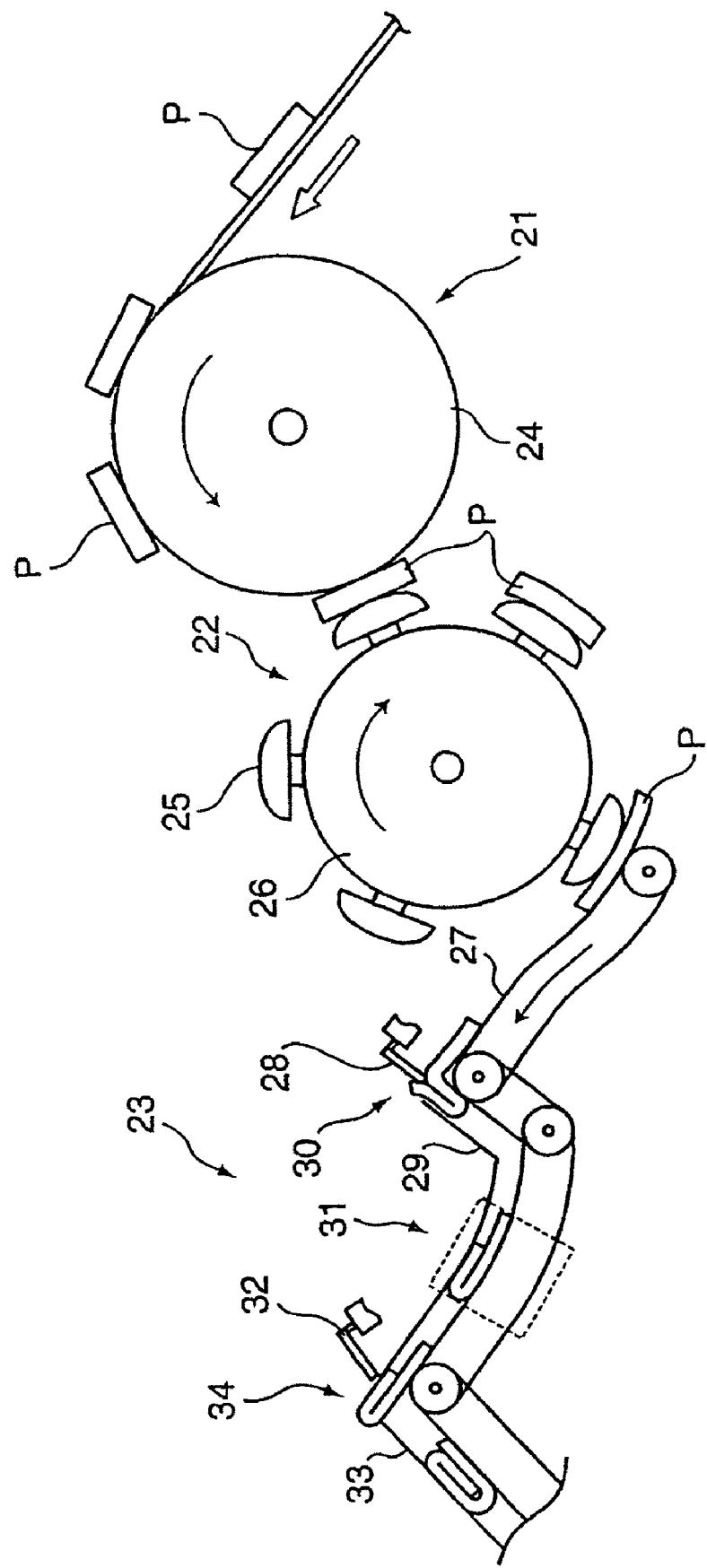
FIG. 3 is a side view showing one exemplary folding apparatus for automatically making the folded disposable pants of the present invention.

FIG. 3 shows one exemplary folding apparatus for automatically folding the disposable pants P. The folding apparatus includes a carry-in mechanism 21 through which the disposable pants P produced by a production apparatus (not shown) is carried in, an inversion mechanism 22 that inverts the convey direction of the carried-in disposable pants P by 90°, and a folding mechanism 23 that sequentially folds the disposable pants P while conveying the same.

Figure 4:
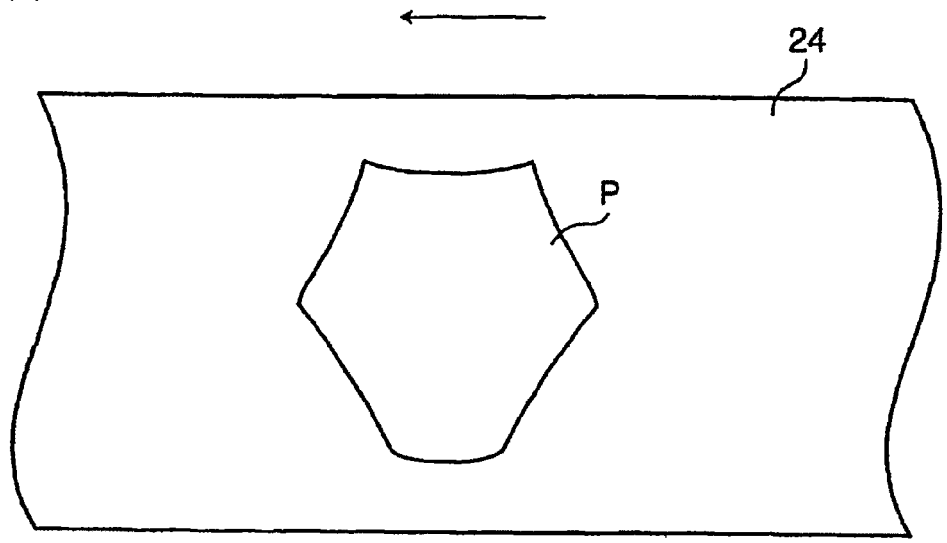
FIG. 4(a) is a plan view showing a conveyance direction of disposable pants on a rotary drum.
FIG. 4(b) is a plan view showing an inverting behavior of the disposable pants on the rotary drum.
Figure 4:
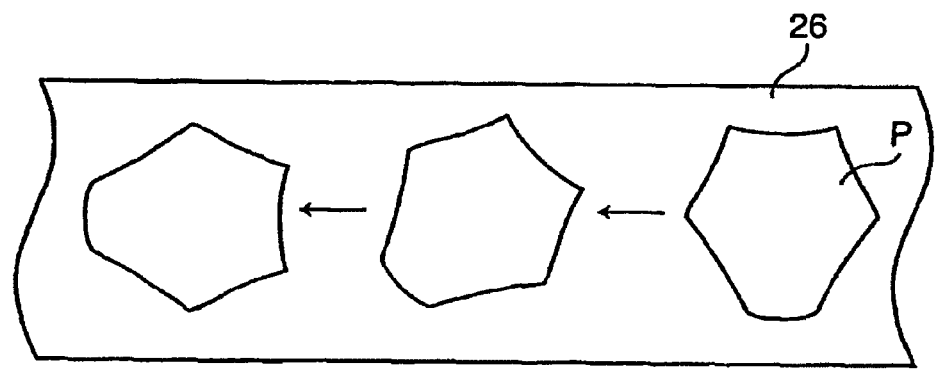

The carry-in mechanism 21 has a rotary drum 24 that carries the disposable pants P into the inversion mechanism 22 while sucking and holding the same depending on the suction force of a vacuum pump or the like, and as shown in FIG. 4(a), laterally conveys the disposable pants P with its lateral side part in the lead.

The inversion mechanism 22 has a counter-rotary drum 26 which is formed in its periphery with a holder 25 that holds the disposable pants P by suction, and inverts the convey direction so that the disposable pants P is conveyed with its bottom part (lower end of the crotch) in the lead as shown in FIG. 4(b), by rotating the holder 25 by 90° by means of a rotation driver.

The folding mechanism 23 has a conveyer 27 that conveys the disposable pants P fed out of the inversion mechanism 22 while sucking the same, a first fold-back section 30 that inserts the disposable pants P in a folded state along the line FL1 into a first guiding portion 29 to fold back the crotch part 5 toward upside of the pants P by pushing an upper part of the crotch part of the disposable pants P along the line FL1 by means of a rotatable pushing rod 28, a second fold-back section 31 that sequentially folds back the right and left lateral parts 6, 8 of the disposable pants P conveyed along the first guiding portion 29 toward the center part 7 by means of right and left fold-back guiding members (not shown), and a final folding section 34 that folds the disposable pants P so that the upper pants part 9 is folded over the lower part 10 by pushing the part that aligns with the end edge of the absorbent main body 4 along the line FL4 by means of a rotatable pushing rod 32 to thereby insert the part aligning with the end edge of the absorbent main body 4 into a second guiding portion 33.

After folding back the crotch part 5 of the disposable pants P upward by means of the first fold-back section 30 of the folding mechanism 23, as shown in FIG. 1(b), the right lateral part 6 of the disposable pants P is folded back toward the center pants part 7, and then the left lateral part 8 is folded thereover by means of the second fold-back section 31, as shown in FIGS. 2(a) and 2(b). Then, in the final folding section 34, as shown in FIG. 2(c), the upper pants part 9 is folded over the lower part 10. Thus, the disposable pants P are automatically folded into a compact folded state.

Then, explanation will be given for a constitution of the folded disposable pants of the present invention. As shown in FIG. 1, a pants shape is formed by providing the outer wear sheet 1 of the disposable pants P with the waist opening W and the leg opening S. To the circumferences of the waist opening W and the leg opening S, the waist elastic member 2 and the leg elastic member 3 are respectively added in an elongated state to give gathers. To each surface side of the outer wear sheet 1 being contactable with wearer's skin, the absorbent main body 4 is adhered.

Figure 5:
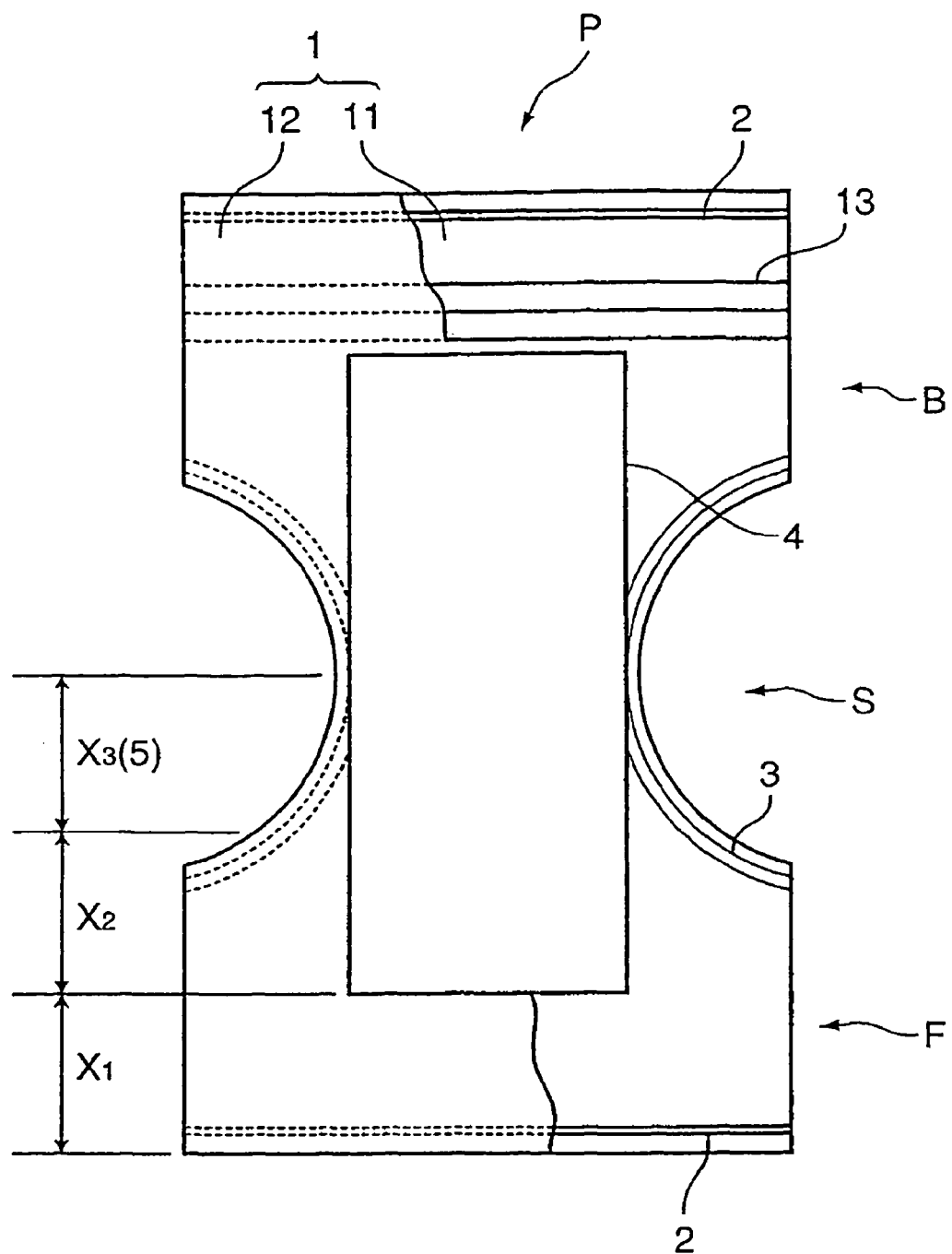
FIG. 5 is a partially cutout development view of the disposable pants shown in FIG. 1.

As is the disposable pants P shown in a developed state in FIG. 5, the outer wear sheet 1 consists of an outermost layer sheet 11 and an inner layer sheet 12, and on each side of the crotch is formed a leg hole part S to form a substantially hourglass shape. The outermost layer sheet 11 and the inner layer sheet 12 are preferably formed of nonwoven fabric from the view point of, for example, feeling to the skin. As such nonwoven fabric, there can be used nonwoven fabrics made of polypropylene, polyethylene, polyester, nylon, and the like, as well as nonwoven fabrics made of composite fibers based on the combinations of polyester/polyester, polyester/polyethylene, polypropylene/polyethylene, and the like.

Between the outermost layer sheet 11 and the inner layer sheet 12, the waist elastic member 2 and the leg elastic member 3, formed of two or more elastic yarns, are sandwiched in an elongated state. Also as shown in the drawing, between the longitudinal end of the absorbent main body 4 and the waist opening end in an upper part of a back side B (back section) of the disposable pants P, preferably, a body fitting elastic member 13 is joined in an elongated state in the same direction with the waist elastic member 2, for improving the fittability of waist. For such elastic members 2, 3, 13, elastic yarns and elastic ribbons can be used. Preferably, the body fitting elastic member 13 is not added to a front side F (front section) of the disposable pants P. This allows easy folding because no contraction force will be exerted.

To the inner layer sheet 12 of the disposable pants P, the absorbent main body 4 is joined. The absorbent main body 4 is preferably rectangular or may be an hourglass shape; however, it is preferably formed into a substantially rectangular shape at least at both longitudinal ends for easy folding. This facilitates the step of folding back the right and left lateral parts of the pants back to the center pants part, and the step of folding back the upper pants part to the lower pants part, while providing the folded pants with rectangular appearance which looks beautiful and facilitates putting the folded pants in a package. In addition, the absorbent main body 4 of rectangular shape is preferred in that the right and left lateral parts of the disposable pants can easily be folded back along the right and left lateral lines of the absorbent main body 4. The corner of each longitudinal end may have a round shape with some degree of roundness.

As already described, the absorbent main body 4 is approximately twice ($x_3+x_2$) as long as the length $x_3$ of the crotch part 5 of the disposable pants P in the front side F. In other words, the entire length of the absorbent main body 4 is approximately two-thirds of the entire length of the disposable pants P. The absorbent main body 4 is preferably adhered to the inner layer sheet 12 so that the length between an end edge in the longitudinal direction thereof and a waist opening end edge, $x_1$, is approximately equal to the $x_3$ or $x_2$.

The use of an ultra-slim absorbent sheet member as the absorbent main body 4 is effective in reducing the thickness of the folded disposable pants P. If the thickness of the absorbent main body 4 of the disposable pants P is 5 mm or smaller, the thickness of the folded pants is also small, resulting in more excellent portability. As such an ultra-slim absorbent sheet member, most suited is an ultra-slim absorbent sheet member using no pulp fiber as disclosed in the WO 01/89439 publication by the present applicant.

Figure 6:
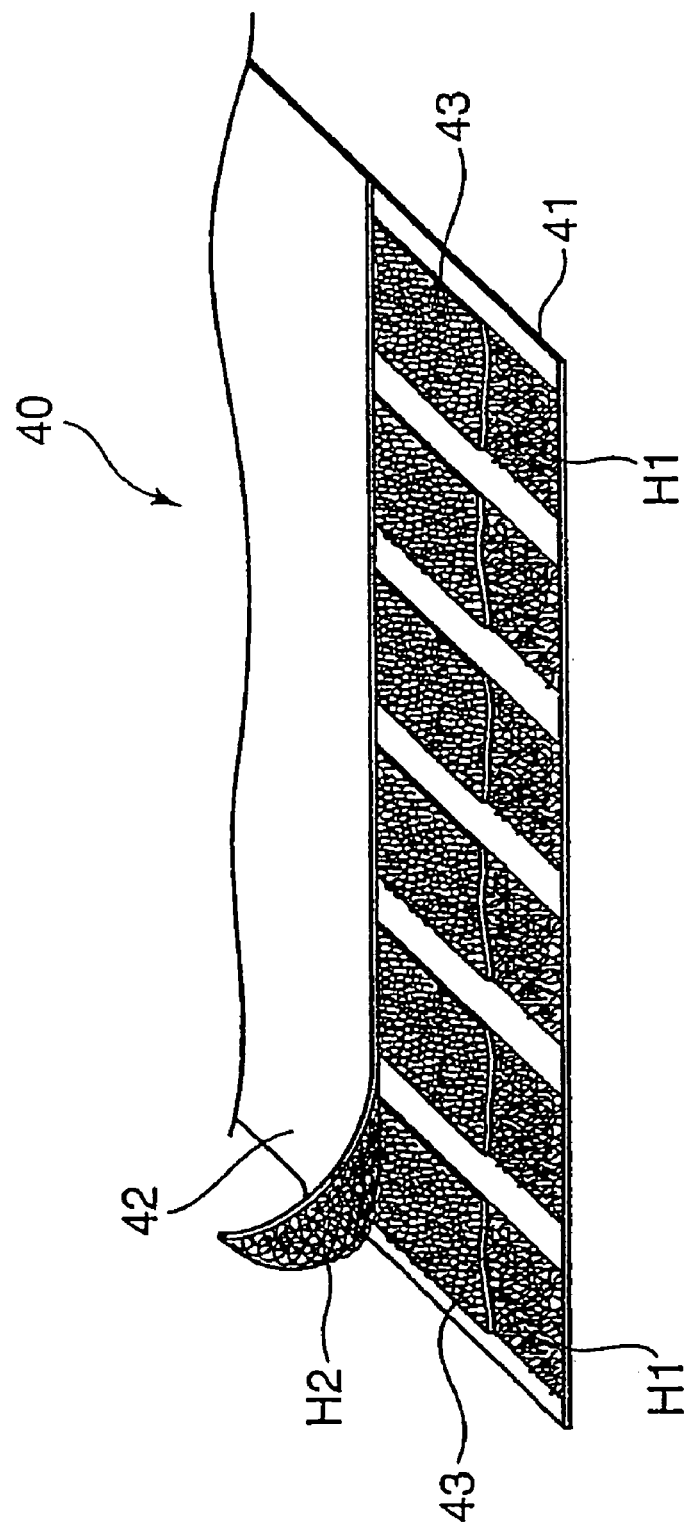
FIG. 6 is a perspective illustrative view of an ultra-slim absorbent sheet member.
Figure 7:
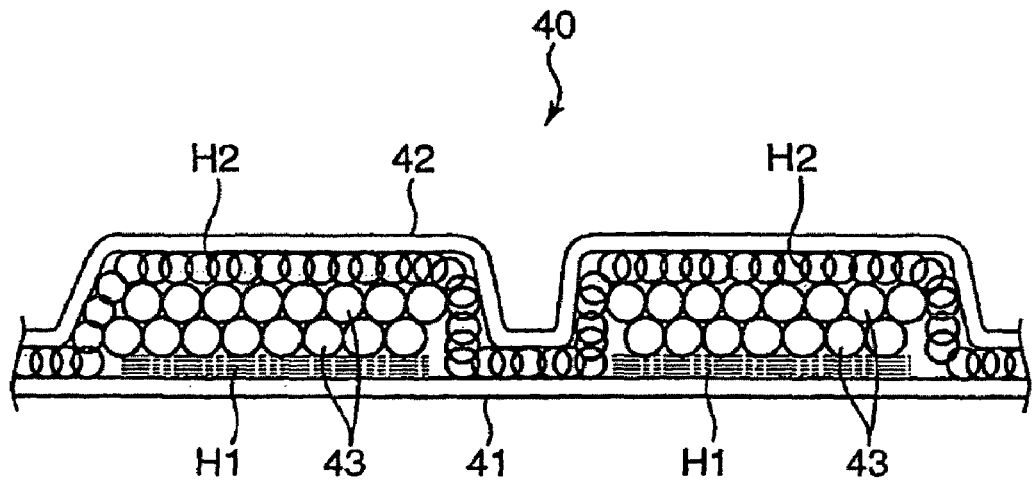
FIG. 7 is a sectional illustrative view of an ultra-slim absorbent sheet member.
Figure 8:
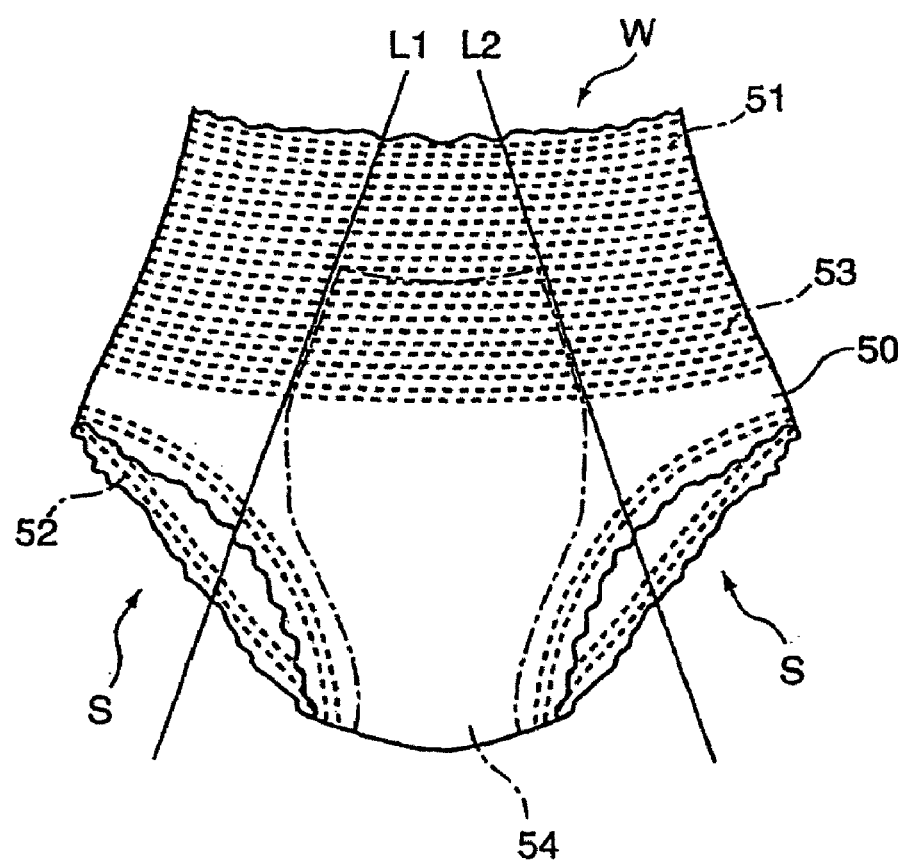
FIG. 8 is a front view of conventional disposable pants.
Figure 9:
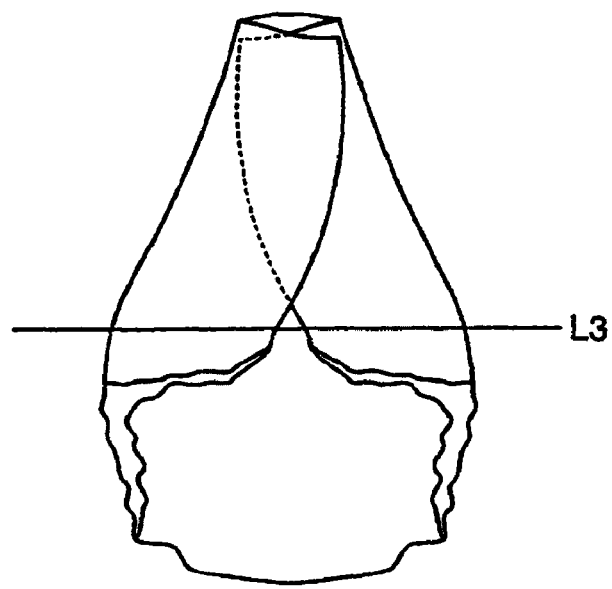
FIG. 9 is a front view showing a folding structure of the conventional disposable pants.
Figure 10:
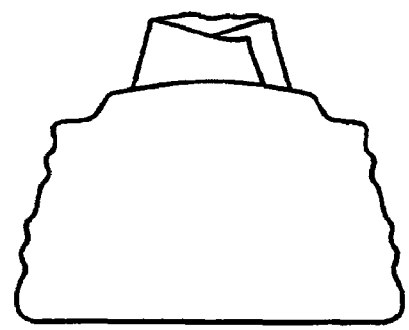
FIG. 10 is a side views showing a folding structure of the conventional disposable pants.
Figure 10:
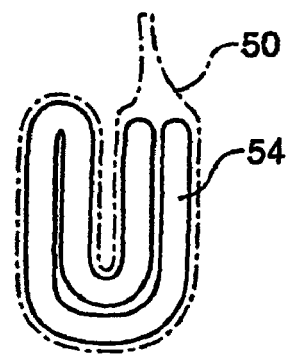

FIG. 6 is a perspective explanatory view of a representative example of the ultra-slim absorbent sheet member 40, and FIG. 7 is a widthwise section view of the one having one third of the width of the ultra-slim absorbent sheet member 40 shown in FIG. 6. The ultra-slim absorbent sheet member 40 is joined between a first nonwoven fabric layer 41 and a second nonwoven fabric layer 42 in such a manner that an absorbent resin powder layer 43 is separated into six strips. The ultra-slim absorbent sheet member 40 will be a very thin absorbent member having a thickness of 5 mm or smaller, because it contains no absorbent fibers such as pulp fibers.

The absorbent resin powder layer 43 is joined between the first nonwoven fabric layer 41 and the second nonwoven fabric layer 42 with a first melt adhesive layer H1 having an area approximately equal to a dispersion area of the absorbent resin powder layer, and a second hot melt adhesive layer H2 formed approximately equal to the entire surface of the second nonwoven fabric layer 42. As to the shape of the dispersion area of the absorbent resin powder layer, although it is not limited to the illustrated example, two or more non-dispersed regions are preferably provided so as to allow rapid dispersion of body fluids and smooth liquid absorption by the absorbent resin powder.

As the absorbent resin powder, there can be used well known absorbent resins, such as polyacrylic acid salt type resins, starch-acrylonitrile type resins, and cellulose type resins. Preferred are those having large absorptivity and exhibiting large liquid absorption speed.

As to the kind of the fiber constituting the first and second nonwoven fabric layers 41, 42, there are preferably used regenerated fibers such as rayon; polyolefins such as polyethylene and polypropylene; synthetic fibers such as polyester; and natural fibers such as silk and pulp (cellulose). There may also be used composite fibers of the core-in-sheath type, the side-by-side type, or the like. In using a hydrophobic fiber, it is desired to carry out any of the well known treatments for making the fiber hydrophilic.

Since the first hot melt adhesive layer H1 is a layer for joining and fixing the absorbent resin powder layer 43 with the first nonwoven fabric layer 42, when the absorbent resin powder is dispersed in a desired pattern, the first hot melt adhesive layer H1 is preferably formed on the first nonwoven fabric layer 41 in the same pattern; while the second hot melt adhesive layer H2 is preferably applied on the entire surface of the second nonwoven fabric layer 42 so as to securely sandwich the absorbent resin powder layer 43 between the first nonwoven fabric layer 41 and the second nonwoven fabric layer 42. These are not limited to the illustrated examples. Joining parts formed by heat sealing or ultrasonic wave may appropriately be provided.

The first hot melt adhesive layer H1 is preferably an web-like member formed by a great number of fine fibers of a hot melt adhesive randomly adhering with one another while leaving gaps, and such an web-like member can be produced using a curtain spray coater in which two or more small discharge ports are arranged in a line and an air spray nozzle capable of blowing off heated air at high speed is provided in the vicinity of each discharge port.

The second hot melt adhesive layer H2 is preferably a mesh member formed of two or more lines of a hot melt adhesive having a spiral locus overlapping with one another while leaving gaps. This is because the second hot melt adhesive layer H2 should be a net member stronger than the first hot melt adhesive layer H1. As a result, it is possible to securely hold and fix the resin particles swollen by liquid absorption between the first nonwoven fabric layer 41 and the second nonwoven fabric layer 42.

Such lines of a hot melt adhesive having a spiral locus can be obtained by using, for example, a spiral spray gun nozzle having three or more air spray nozzles which are located symmetrically with respect to a point in the vicinity of a hot melt discharge port and capable of blowing off air in the center direction of the nozzle.

The first and the second hot melt adhesives may be either the same or different kinds, and their kinds are not particularly limited. From the view point of productivity, those melting at about 60° C. to 180° C. are preferred, and there are preferably used styrene type elastomers such as SIS, SIBS, SEBS, and SEPS; ethylene-vinyl acetate type copolymers; polyester, acryl or polyolefin type elastomers; and rubbers such as polyisobutylene, butyl rubber, polyisoprene, and natural rubber. Preferred are those easy to elongate for securely fixing the swollen particles after liquid absorption, and in this point, preferred are styrene type elastomers and rubbers.

When the above ultra-slim absorbent sheet member 40 is used as the absorbent main body 4, a liquid-impermeable sheet which is as the approximately same size as or slightly larger than the ultra-slim absorbent sheet member 40 may be used as a back sheet, the ultra-slim absorbent sheet member 40 may be joined thereon, and well known members such as a liquid-permeable top sheet, spatial gathers, and the like, may be provided, if necessary.

Besides the ultra-slim absorbent sheet member 40 of the above-described structure, an absorbent sheet member in which either the first nonwoven fabric layer 41 or the second nonwoven fabric layer 42 is omitted, or an absorbent sheet in which absorbent resin powder is mixed at a step for the production of a nonwoven fabric, may also be used as an absorbent member of the absorbent main body 4. Other constituents well known by those skilled in the art may also be added.

According to the present invention, it is possible to fold the disposable pants into a substantially quadrilateral having a length of about one third of the entire length of the front section (or back section) of the disposable pants P before folded, and a width of about one third of the maximum width of the pants P. Such compactly folded quadrilateral provides excellent portability. Furthermore, since the folded quadrilateral product has generally even thickness, when two or more products are packed into a package, they can easily be clipped and superior in handling ability. The resultant package looks beautiful because the package is neat and flat at every side.

In addition, by using the ultra-slim absorbent sheet member as the absorbent main body, it is possible to make the thickness of the quadrilateral product after folding as small as 3 cm or less, and a great number of products can be packed in a package, leading to a reduction in storage cost and transport cost. Furthermore, the disposable pants of the present invention are those having a thickness suited for folding, which are easy to fold, realize thick and compact profile after folding and are superior in portability.

What is claimed is:

1. A Method for folding disposable pants,
the disposable pants comprising an outer wear sheet of pants shape, and an absorbent main body adhered to a skin-contactable surface side of the outer wear sheet and having a substantially rectangular shape at least both ends in a longitudinal direction of the absorbent main body, comprising:
conveying the disposable pants with a crotch part in the lead;
pushing the crotch part by a rod to fold back the crotch part toward a center part of the disposable pants:
folding back right and left lateral parts of the disposable pants toward the center part by right and left fold-back guiding members; and
pushing a part along an end edge of the absorbent main body by a rod to fold back an upper part over the crotch part.

2. The method for folding disposable pants according to claim 1, wherein
the absorbent main body has a substantially rectangular shape, and
the right and left parts of the disposable pants is folded back along right and left lateral lines of the absorbent main body.

3. The method folding disposable pants according to claim 1, wherein the absorbent main body has a thickness of 5 mm or smaller.

4. The method for folding disposable pants according to claim 1, wherein the absorbent main body is adhered to the outer wear sheet so that a length between a lowermost end of the crotch part of the disposable pants and a longitudinal end of the absorbent main body is approximately twice the length between the longitudinal end of the absorbent main body and an end of a waist opening of the disposable pants.

5. The method for folding disposable pants according to claim 1, wherein the disposable pants are folded into approximately one third of the length between the end of the waist opening and the lowermost end of the crotch part of the disposable pants.

6. The method for folding disposable pants according to claim 1, wherein:
a waist elastic member is added to the circumference of the waist opening in front and back sections of the disposable pants;
a body fitting elastic member is added in a same direction as the waist elastic member only between the longitudinal end of the absorbent main body and the waist elastic member in the back section of the disposable pants; and
no elastic member is added between an opposite longitudinal end of the absorbent main body and the waist elastic member in the front section of the disposable pants.

* * * * *